United States Patent [19]
Golub

[11] Patent Number: 5,954,703
[45] Date of Patent: *Sep. 21, 1999

[54] METHOD AND APPARATUS FOR APPLYING 5-AMINOLEVULINIC ACID

[75] Inventor: Allyn Golub, Miramar, Fla.

[73] Assignee: Dusa Pharmaceuticals, Inc., Ontario, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/962,294

[22] Filed: Oct. 31, 1997

[51] Int. Cl.$^6$ ................................. A61M 35/00
[52] U.S. Cl. .................... 604/290; 604/289; 604/310
[58] Field of Search .................... 604/289, 290, 604/306, 309, 310, 88, 89, 91, 93; 424/448, 449, 485, 486–488; 514/772.6, 781, 782

[56] References Cited

U.S. PATENT DOCUMENTS

| D. 272,091 | 1/1984 | Kaufman | D24/34 |
| D. 377,978 | 2/1997 | Haber | D24/119 |
| 2,195,675 | 4/1940 | Lewis | 128/261 |
| 3,324,855 | 6/1967 | Heimlich | 128/269 |
| 3,876,314 | 4/1975 | Nehring | 401/133 |
| 3,891,331 | 6/1975 | Avery | 401/132 |
| 4,578,055 | 3/1986 | Fischer | 604/2 |
| 4,838,851 | 6/1989 | Shabo | 604/1 |
| 4,850,729 | 7/1989 | Kramer et al. | 401/183 |
| 4,925,327 | 5/1990 | Wirt | 401/205 |
| 5,019,033 | 5/1991 | Geria | 604/2 |
| 5,098,297 | 3/1992 | Cheri | 433/215 |
| 5,171,149 | 12/1992 | Alpert | 433/217.1 |
| 5,490,736 | 2/1996 | Haber | 401/40 |

FOREIGN PATENT DOCUMENTS

26 39 346  3/1977  Germany.
2 204 365  11/1988  United Kingdom.

OTHER PUBLICATIONS

DUSA Pharmaceuticals, Inc., 1996 Annual Report, Apr. 15, 1997.

SEC Form 10K submitted by DUSA Pharmaceuticals, for the fiscal year ended Dec. 31, 1996. Filed Mar. 24, 1997.

*Primary Examiner*—John G. Weiss
*Assistant Examiner*—David J. Cho
*Attorney, Agent, or Firm*—Foley & Lardner

[57] ABSTRACT

A method and apparatus for storing, mixing and applying ALA as a treatment for lesions. The apparatus comprises a deformable container enclosing a hermetically sealed compartment of essentially anhydrous ALA which is shielded from exposure to air and moisture, and a liquid diluent. The liquid diluent may be in a second compartment. The deformable container is squeezed to crush the compartments and mix the essentially anhydrous ALA with the liquid diluent. The ALA may be delivered from the deformable container through a point applicator for controlling and precisely directing the application during treatment.

19 Claims, 2 Drawing Sheets

METHOD AND APPARATUS FOR APPLYING 5-AMINOLEVULINIC ACID

BACKGROUND OF THE INVENTION

1. Field of the Invention

The present invention relates to an apparatus and method for supplying, mixing and applying 5-aminolevulinic acid, also known as 5-amino-4-oxo-pentanoic acid (hereinafter referred to as ALA), in a simple, cost effective manner. More particularly, the present invention relates to a method and apparatus for supplying a two component system comprising ALA and a liquid diluent, wherein the two components are inhibited from contact with each other, as well as contact with light, moisture and air, until just prior to use, when they are mixed. Topically applied ALA, in association with irradiation with light, has been clinically tested in the treatment of pre-cancerous lesions such as actinic keratosis.

2. Description of Related Art

It is known that ALA is degraded in aqueous solution. The inventor has further found that ALA turns brown, and presumably is degraded, in all sorts of topical vehicles such as creams, ointments and solid vehicles. Thus the inventor found it necessary to employ a means to store ALA until ready for treatment in topical applications, as well as to mix the ALA just prior to use, and to focus the area of application to the skin.

In the field of dentistry, U.S. Pat. No. 5,171,149 to Alpert discloses the use of crushable glass ampules for the application of at least one dentin conditioner onto teeth. Glass ampules are provided in a tube with an open applicator at one end. The ampules are crushed to allow the tube contents to flow out of the applicator to prepare the dentin surface of teeth for bonding.

U.S. Pat. No. 5,490,736 to Haber et al. (hereinafter referred to as Haber) discloses a topical applicator having a barrier interposed between a dry medication and a diluent. The barrier, which partitions an applicator body shared in common by the medication and diluent, is ruptured or displaced by pressure on the applicator body. Haber discloses several means for exposing a medicine saturated swab within the applicator body for topical treatment of acne.

Although it is known that ALA degrades in moisture, the present inventor knows of no prior art methods of storing, mixing and applying ALA via a single device which prevents degradation by moisture, other than storage of the ALA in an anhydrous environment.

SUMMARY OF THE INVENTION

Degradation of ALA begins immediately upon exposure to moisture containing air, hence its storage and application must be strictly controlled. It is an object of the present invention to provide a simple, cost effective method of storing, mixing with a liquid diluent just prior to use, and applying ALA.

It is a further object of the present invention to provide an apparatus for storing, mixing and applying ALA, wherein the ALA is limited in exposure to air until just prior to use. The ALA applicator according to the present invention allows storage of the ALA for long periods of time by hermetically sealing essentially anhydrous ALA in the applicator, thus separating the ALA and other components from each other and minimizing exposure to moisture and air, before mixing the components and then applying them to the skin.

It is yet a further object of the present invention to provide a disposable ALA applicator for providing controlled administration of ALA in a topical treatment for rapidly growing normal and abnormal cells, e.g. skin cancer or pre-cancerous lesions.

These and other objectives are achieved by the present invention by providing a method and apparatus for storing and applying ALA from a hermetically sealed, essentially frangible compartment enclosed in a deformable container also containing separately a liquid diluent. In this case, frangible includes any arrangement which releases the contents of a compartment by disrupting the form of the compartment. Preferably, the essentially frangible compartment comprises a glass ampule or vial. Squeezing the container disrupts, e.g. crushes, the compartment (or compartments if the liquid diluent is similarly contained), allowing the ALA and liquid diluent components to mix just prior to use. The ALA is controllably applied directly onto a topical surface by a point applicator portion of the container.

Preferably, the topical surface is an external surface such as the skin. However, internal surfaces such as vaginal, rectal, or oral surfaces may also be treated according to the present invention.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

DETAILED DESCRIPTION OF THE PREFERRED EMBODIMENTS

Figure 1:
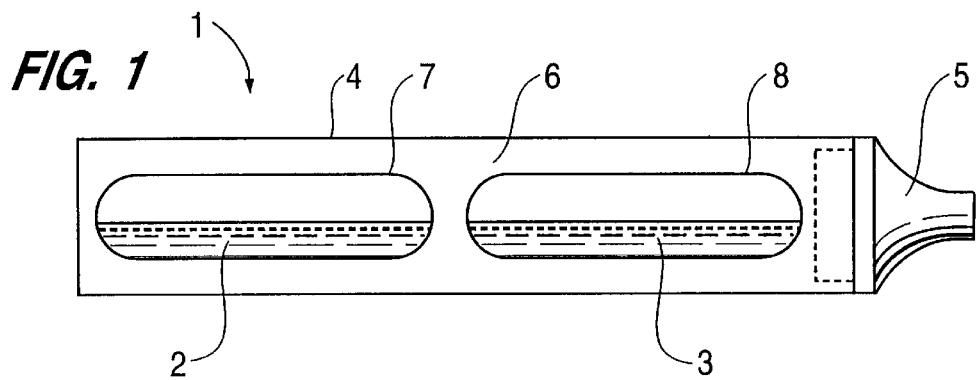
FIG. 1 shows an embodiment of an ALA applicator according to the present invention.

FIG. 1 is an exemplary embodiment according to the present invention showing an applicator apparatus 1 which comprises two separate essentially frangible compartments 7,8 within a deformable container 4. One compartment 8 contains essentially anhydrous ALA 3 and the other compartment 7 contains a liquid diluent 2 for the essentially anhydrous ALA 3. The container 4 has a point applicator 5 provided at one end thereof. Preferably, the compartment 8 containing the essentially anhydrous ALA 3 is relatively proximate to the point applicator 5, and the compartment 7 containing the liquid diluent 2 is relatively distant to the point applicator 5. The point applicator 5 may be removably insertable into the container 4 to facilitate manufacture of the applicator. An air space 6 may also be provided within the deformable container 4. The container 4 is preferably made of a plastic material which is deformable enough so that when squeezed its side walls can contact side walls of the essentially frangible compartments 7,8 and exert enough pressure to release the contents, e.g. by crushing, from the compartments 7,8. The container 4 must also be resistant to interaction with ALA. The container 4 is preferably composed of low density polyethylene (LDPE), however, high density polyethylene, polypropylene, butyrate or propylene copolymers and other equivalent materials may also be used. Disrupting the compartment 7 releases the liquid diluent 2 into the deformable container 4. Thereafter, disrupting the compartment 8 releases the essentially anhydrous ALA 3 which dissolves in the liquid diluent 2 in the deformable container 4 before being distributed through the point applicator 5. The deformable container 4 is resistant to puncture and preferably resistant to scoring, such as from broken glass fragments resulting from crushing compartments 7,8.

The ALA 3 is essentially anhydrous, which means that it contains no more water than would permit degradation of the ALA 3 under normal conditions of use or storage, typically one to two years or more. Preferably, the ALA 3 and its environment are water free.

One particularly useful diluent used in conjunction with the applicators of the present invention is an alcohol/water solution. The solution may also comprise a wetting agent and/or a humectant. A range of weight/weight percentages for a preferred solution are 39.9–48.8 Alcohol (USP or SDA 40–2), 39.1–47.8 Purified Water USP, 5.9–7.4 LAURETH-4, 3.5–4.3 Isopropyl Alcohol USP, and 1.5–1.8 Polyethylene Glycol 400 NF. The weight/weight percentages of a particularly preferred diluent are 44.37 Alcohol (USP or SDA 40–2), 43.46 Purified Water USP, 6.59 LAURETH-4, 3.93 Isopropyl Alcohol USP, and 1.65 Polyethylene Glycol 400 NF. It is envisioned that various other alcohol/water percentages could be used, various surfactants could be substituted for the LAURETH-4 (e.g. sodium lauryl sulfate, as well as other ionic or non-ionic surfactants), and propylene glycol or glycerin could be substituted for the polyethylene glycol.

The compartments 7,8 may contain just enough essentially anhydrous ALA 3 and diluent 2 for a single topical treatment of a lesion, e.g. a pre-cancerous lesion on the skin. Since the ALA has a short useful life of less than 24 hours after exposure to air and moisture, aliquots in excess of that which would be used in a single treatment would be wasted. Preferably, only as much ALA as a practitioner would use during a single treatment is provided within each applicator. Volumes from less than $1/10$ of a cubic centimeter to more than a cubic centimeter of ALA solution may be held within the container 4. The essentially anhydrous ALA 3 and diluent 2 are provided in predetermined proportions, usually in an approximate 1:1 ratio.

After supplying the compartment 8 with the essentially anhydrous ALA 3, the compartment 8 may be topped with nitrogen, an inert gas, or evacuated before being hermetically sealed. Hermetic sealing of compartment 8 is important to prevent exposing the essentially anhydrous ALA 3 to air, moisture or the diluent 2, which would degrade the essentially anhydrous ALA 3. Generally, hermetic sealing results in less than 0.5% water and 1% oxygen in the compartment 8, and preferably less than 0.05% water and 0.1% oxygen, and more preferably less than 0.005% water and 0.01% oxygen.

Figure 2:
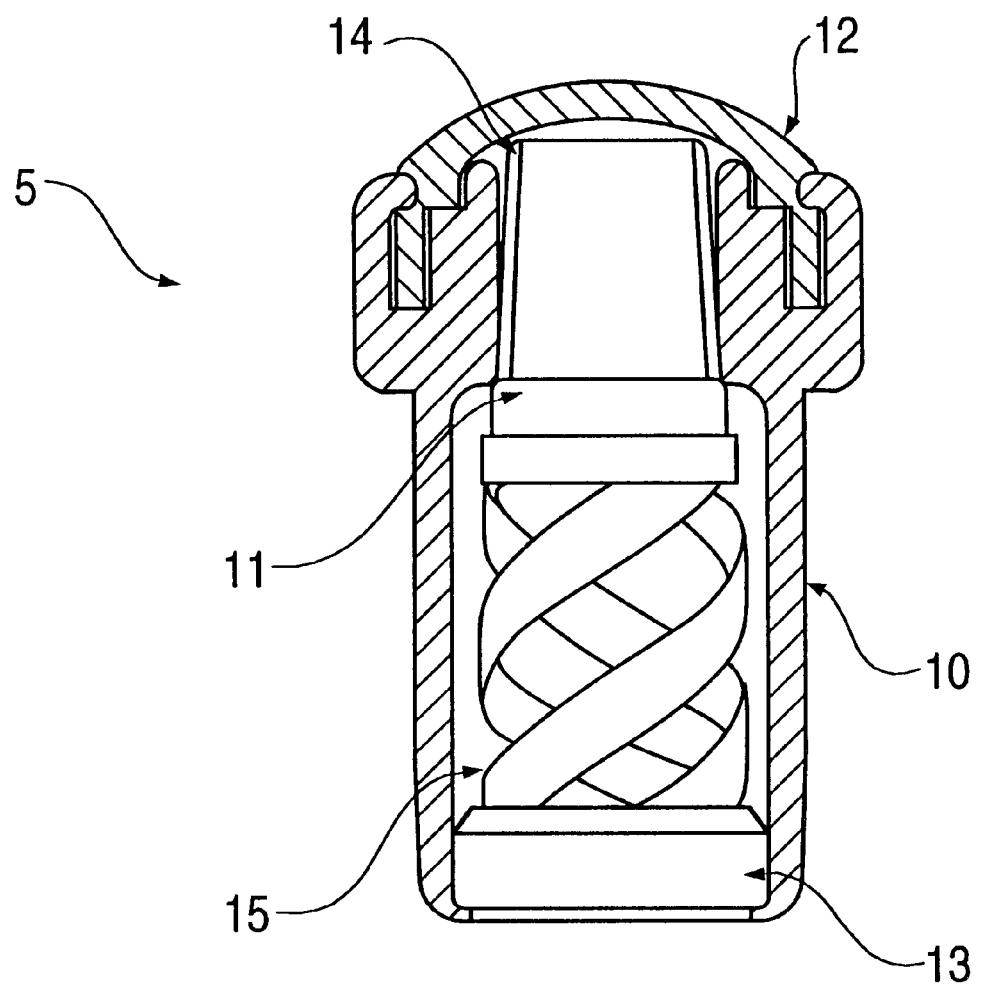
FIG. 2 shows an embodiment of a point applicator according to the present invention.

The container 4 includes a point applicator 5 occluding the dispensing end of the container 4. FIG. 2 shows a preferred point applicator 5 according to the present invention for controlling the distribution of ALA directly on an afflicted portion of a patient's skin. In practice, distribution control is proportional to the amount of force a practitioner uses pressing the point applicator 5 against the topical surface. According to a preferred embodiment, approximately 1–2 $mg/cm^2$ of ALA admixed with approximately 10–20 $\mu l/cm^2$ of diluent is distributed. Treatment is most effective when the point applicator 5 distributes a quantity of the ALA solution which is at least sufficient with respect to the lighting conditions during subsequent irradiation with light.

The preferred point applicator 5 illustrated in FIG. 2 comprises a tubular body 10 configured to receive a resiliently biased valve 11 and a liquid permeable cover 12. The tubular body 10 includes an outer cylindrical surface adapted to matingly engage a corresponding inner cylindrical surface of the container 4. The valve 11 is received within an inner cylindrical surface of the tubular body 10. Although a coil type spring 15 is shown biasing the valve 11 against the tubular body 10, any equivalent resilient element can be substituted for the coil type spring 15. Cover 12 is secured over the outlet end of the tubular body 10. At least one filter element 13 ensures that any particles of the disrupted compartments 7,8 are maintained within the container 4.

A hollow element 14 generally extends between the cover 12 and the valve 11. The force exerted by the practitioner pressing the exterior surface of the cover 12 against a lesion displaces hollow element 13, which in turn creates a gap between the valve 11 and the tubular body 10 through which ALA may flow to the cover 12. The maximum size of the gap is a function of the length of the hollow element 13.

Many alternatives to the preferred point applicator 5 illustrated in FIG. 2 are envisioned, including a dropper tip, a cotton tip, or a nylon tip.

Figure 3:
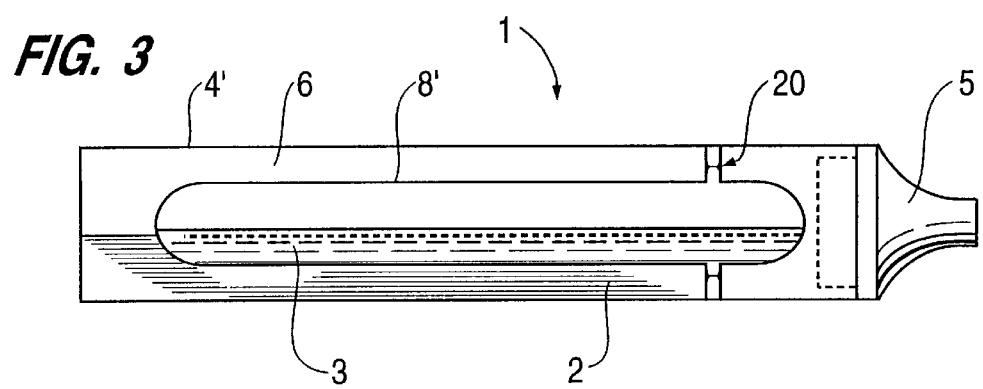
FIG. 3 shows an alternate embodiment of an ALA applicator according to the present invention.

An alternate embodiment of an applicator 11 according to the present invention is shown in FIG. 3. A container 4' similarly encloses at least one compartment 8' which contains essentially anhydrous ALA 3. However, the liquid diluent 2 is not contained within a separate compartment as discussed with respect to FIG. 1. Instead, the liquid diluent 2 is contained directly within the container 4' by means of a seal 20 interposed between the compartment 8' and the container 4'. A two part seal 20 is shown with a raised annular rib on the inner cylindrical surface of the container 4' matingly engaging a corresponding raised annular rib on the outer surface of the compartment 8'. It is noted that a number of variations are envisioned including a one part seal formed on one of the outer surface of the compartment 8' or the inner cylindrical surface of the container 4', and reversing the locations of the essentially anhydrous ALA 3 with the liquid diluent 2.

According to a preferred technique for using the present invention, the applicator apparatus 1 is held upright with the point applicator 5 pointing up. With a cardboard sleeve (not shown) surrounding the deformable container 4, the diluent compartment 7 (if present) is first disrupted releasing the diluent 2, then the ALA compartment 8(8') is disrupted to release the essentially anhydrous ALA 3. While maintaining the applicator apparatus 1 in the upright position, the applicator apparatus 1 is shaken for approximately three minutes to completely dissolve the essentially anhydrous ALA 3 in the liquid diluent 2. The applicator apparatus 1 is now ready for treatment, and the solution should be applied immediately after admixture. The applicator apparatus 1 is tilted to so that the ALA topical solution flows toward the point applicator 5. ALA topical solution distribution is accomplished by pressing and releasing the point applicator 5 against the lesions to be treated. Preferably, the lesion, and not the surrounding skin, is uniformly wetted and then allowed to dry. After the original application has dried, the treatment may be repeated, preferably for a total of two applications.

One method of treating patients with ALA according to the present invention includes providing a ALA applicator as described above, deforming the deformable container so as to exert enough force to first crush the diluent compartment then the ALA compartment, admixing the ALA and diluent, and dispensing the ALA from the point applicator.

According to a preferred method of treatment, immediately prior to administration, the essentially anhydrous ALA 3 and liquid diluent 2 are admixed by crushing glass compartments 7,8 (or glass compartment 8') in the deformable container 4. Shaking the deformable container 4(4') dissolves the essentially anhydrous ALA 3 in the liquid diluent 2. The resulting ALA topical solution is applied directly to target actinic keratosis lesions by gentle dabbing with the point applicator 5. The ALA topical solution is applied in sufficient volume to uniformly wet the lesion surface, without excess running or dripping. Once the initial application has dried, a second application may be made in the same manner to assure that complete and uniform coverage of the lesion surface has been accomplished.

In a preferred embodiment, the ALA topical solution contains alcohol and dries quickly after application. Therefore, the ALA topical solution is carefully applied with the point applicator 5 only to skin areas to be treated, in a quantity adequate to wet the area thoroughly, but not enough to allow dripping or running. The solution is applied, allowed to dry, applied again and allowed to dry before proceeding. Prior to subsequent irradiation with light, the surface of all treated lesions may be rinsed with water to remove residual ALA and allowed to dry.

The methods and apparatus according to the present invention are also useful for other applications of ALA to flora and fauna in addition to the treatment of humans.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A method of storing, mixing and applying 5-aminolevulinic acid which inhibits exposure of the 5-aminolevulinic acid to air and moisture until just prior to application, said method comprising:

hermetically sealing essentially anhydrous 5-aminolevulinic acid within a first essentially frangible compartment;

disposing said first compartment within a deformable container, said container having an applicator;

deforming said container to crush said first compartment and mix said essentially anhydrous 5-aminolevulinic acid with a liquid diluent in said container; and topically applying 5-aminolevulinic acid from said container through said applicator.

2. The method as defined in claim 1, wherein said applicator comprises a point applicator for controlling topical application of 5-aminolevulinic acid.

3. The method as defined in claim 1, further comprising:

sealing said liquid diluent in a second essentially frangible compartment; and, disposing said second compartment within said container.

4. The method as defined in claim 3, wherein said step of deforming said container crushes said second compartment prior to crushing said first compartment.

5. A method of treating rapidly proliferating cells with 5-aminolevulinic acid, said method comprising:

providing a deformable container containing a first essentially frangible compartment of essentially anhydrous 5-aminolevulinic acid and a second essentially frangible compartment of a liquid diluent, said essentially anhydrous 5-aminolevulinic acid being hermetically sealed in said first compartment;

deforming said container to crush said first and second compartments within said container;

mixing said essentially anhydrous 5-aminolevulinic acid and said liquid diluent; and topically applying 5-aminolevulinic acid to the rapidly proliferating cells.

6. The method as defined in claim 5, wherein said topical application of 5-aminolevulinic acid is controlled by a point applicator.

7. An applicator for dispensing 5-aminolevulinic acid, said applicator comprising:

a first essentially frangible compartment containing essentially anhydrous 5-aminolevulinic acid;

a deformable container enclosing said first compartment and a liquid diluent for 5-aminolevulinic acid; and a topical applicator dispersing 5-aminolevulinic acid from said container;

wherein said first essentially frangible compartment is interposed between said liquid diluent and said topical applicator.

8. The applicator as defined in claim 7, wherein said first compartment is essentially hermetically sealed.

9. The applicator as defined in claim 7, further comprising:

a second essentially frangible compartment containing said liquid diluent, said deformable container enclosing said second essentially frangible compartment.

10. The applicator as defined in claim 7, wherein said topical applicator includes a point applicator for controlling dispersion of 5-aminolevulinic acid from said container.

11. The applicator as defined in claim 10, wherein said point applicator includes:

a tubular body having an inner cylindrical surface and an outer cylindrical surface, said outer cylindrical surface contiguously confronting an inner cylindrical surface of said container;

a resiliently biased valve for normally occluding a first end of said tubular body; and a liquid permeable cover for covering said first end of said tubular body;

wherein depressing said cover creates a gap between said valve and said tubular body for distributing the 5-aminolevulinic acid.

12. The applicator as defined in claim 11, further comprising:

a seal interposed between said first essentially frangible compartment and said container.

13. The applicator as defined in claim 12, wherein said seal includes a raised annular rib on at least one of said tubular body outer surface and said container inner cylindrical surface.

14. The applicator as defined in claim 7, wherein said liquid diluent comprises an alcohol/water solution.

15. The applicator as defined in claim 14, wherein said liquid diluent further comprises a wetting agent.

16. The applicator as defined in claim 15, wherein said wetting agent is a surfactant.

17. The applicator as defined in claim 14, wherein said liquid diluent further comprises a humectant.

18. The applicator as defined in claim 17, wherein said humectant is a polyalcohol.

19. The applicator as defined in claim 17, wherein said humectant is selected from the group consisting of polyethylene glycol, propylene glycol and glycerin.

* * * * *